United States Patent [19]
Mansfield et al.

[11] Patent Number: 6,019,896
[45] Date of Patent: Feb. 1, 2000

[54] METHOD FOR USING A QUALITY METRIC TO ASSESS THE QUALITY OF BIOCHEMICAL SEPARATIONS

[75] Inventors: Elaine S. Mansfield, Sunnyvale; Lian-She Zhao; Marina Vainer, both of Fremont; Curtis R. Kautzer, San Jose, all of Calif.

[73] Assignee: Molecular Dynamics, Inc., Sunnyvale, Calif.

[21] Appl. No.: 09/036,767

[22] Filed: Mar. 6, 1998

[51] Int. Cl.7 .............................. B01D 15/08; C12Q 1/68; C12P 19/34; G01N 30/00
[52] U.S. Cl. ...................... 210/198.2; 435/6; 435/91.1; 435/91.2; 210/198.3; 73/61.52
[58] Field of Search .................. 435/6, 91.1, 91.2; 210/198.2, 198.3; 73/61.52

[56] References Cited

U.S. PATENT DOCUMENTS

| | | | |
|---|---|---|---|
| 5,039,409 | 8/1991 | Blaffert et al. | 210/198.2 |
| 5,558,998 | 9/1996 | Hammond et al. | 435/6 |
| 5,580,728 | 12/1996 | Perlin | 435/6 |
| 5,604,097 | 2/1997 | Brenner | 435/6 |

OTHER PUBLICATIONS

Baker et al Capillary Electrophoresis pp. 200–210, 1995.
Holgersson et al Electrophoresis vol. 5, pp. 890–895, 1995.
David C. Mansfield et al., "Automation of Genetic Linkage Analysis Using Fluorescent Microsatellite Markers", *Genomics*, vol. 24, pp. 225–233 (1994).
Roland Stoughton et al., "Data–adaptive algorithms for calling alleles in repeat polymorphisms", *Electrophoresis*, vol. 18, pp. 1–5 (1997).

*Primary Examiner*—Bradley Sisson
*Assistant Examiner*—Jeffrey Siew
*Attorney, Agent, or Firm*—Thomas Schneck

[57] ABSTRACT

A method for performing separation assays of biochemical samples includes computing a quality metric based on peak data produced during the separation run. The quality metric is the basis for selecting a subsequent step in the assay, including whether to re-run the separation when the quality metric indicates a low quality separation run. In a preferred embodiment, the quality metric is computed based on a peak resolution metric indicative of the peak resolution of the sample peaks in the data and a signal-to-noise ratio of the data. When a co-migrating standard is included in the separation run, the quality metric is further based on the degree of migration linearity of the reference peaks produced by the standard. The method was reduced to practice in separations to size and sort DNA fragments in high-throughput capillary array electrophoresis separations.

21 Claims, 7 Drawing Sheets

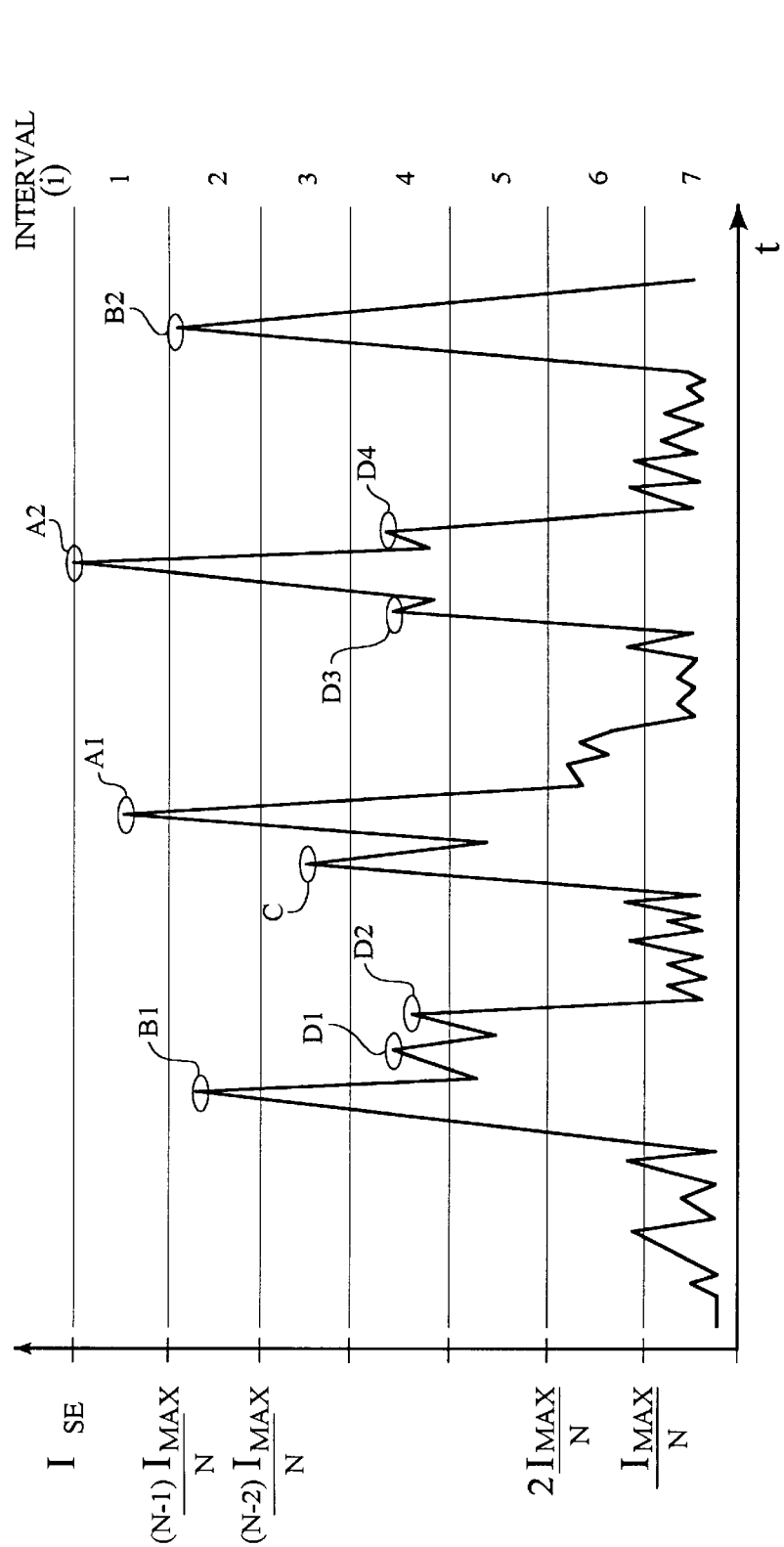
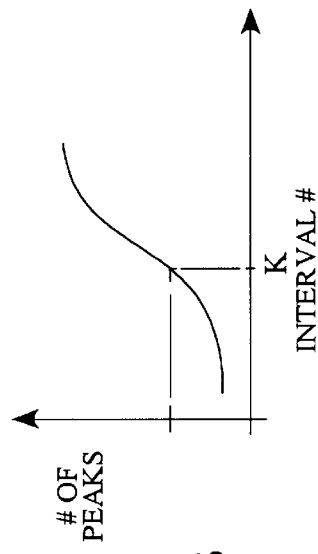
Fig. 5B
Fig. 5A

METHOD FOR USING A QUALITY METRIC TO ASSESS THE QUALITY OF BIOCHEMICAL SEPARATIONS

TECHNICAL FIELD

The present invention relates to a method for biochemical separations in general and more specifically to the use of quality metrics to assess the quality of the separation of DNA fragments.

BACKGROUND OF THE INVENTION

Biochemical separations play an important role in the analytical study of countless complex biological, environmental, and industrial samples. Separation procedures reveal the constituent components in a sample, thus shedding some light on our understanding of the nature and purity of things. Separation methods are simply tools by which we increase the quantity of information available about complex mixtures and to enhance the quality of that information. Most complex mixtures, especially those of biochemical origin, contain similar underlying structures and common functional groups. Thus, it is difficult if not impossible to identify or quantify the constituents so long as they remain in the mixture. By separating out the constituents in a mixture, their identification can be made such as by detecting a physical property; e.g. light absorbance, size, mass tag, presence of color tag, etc.

Biochemical separation techniques are used in a variety of the life sciences and related industries, including: nutritional analysis of foods for protein, fatty acid content, and carbohydrate content; analysis of foods for toxins, e.g. bacterial contamination or shellfish poisons; protein analysis, including gel electrophoresis and protein purification; separation of carbohydrates, separation of oligonucleotides and individual molecules such as nucleotides, amino acids, sugars, and biogenic amines; separation and analysis of pesticides and other synthetic organic molecules; analysis of drugs and pharmaceuticals; clinical profiling such as serum protein analysis; forensic and explosive analysis; analysis of serum organic acids, cyanide and related compounds, and chemical warfare compounds; urinalysis for drug metabolites; analysis of neurotransmitters such as catechol amines and epinephrine; separation and analysis of lipoproteins, separation and analysis of vitamins; preparation or purification of monoclonal antibodies; and protein digest sequencing or structural analysis. The list of course is not exhaustive and is intended to point out the large number of applications and diverse uses for separation methodologies.

Manual inspection of the separation data which results from a separation procedure is a labor intensive and time consuming effort. It is prone to error because of the repetitiveness of the process, and is subject to inconsistent results because of the reliance on subjective human interpretation of the data. This is generally true of all separation data regardless of the source of the data, i.e. whether the data comes from an electrophoretic separation or a chromatographic process, and regardless of the nature of the biochemical analytes being studied.

One of the most common uses of biochemical separation is in the analysis of DNA, and one of the greatest undertakings in this area is the Human Genome Initiative. Genetic analysis projects can require thousands, even millions, of DNA genotypes to be determined, analyzed, and reviewed. For example, it is estimated that up to one million genotypes will be required to map multigenic disorders such as diabetes and heart disease.

Genetic mapping plays an essential role in the process of gene discovery. Armed with new genetic markers and maps, researchers are poised to localize new genes at a dramatic pace. The most commonly used genetic markers employed in gene linkage analysis are highly informative, simple sequence repeat (SSR) polymorphisms. Currently, these 2-, 3-, and 4-base pair (bp) repeats are genotyped by manual inspection and scoring of electropherogram profiles generated on slab-gel electrophoresis systems. For example, Mansfield et al. disclose a method for automatically computing the lengths of DNA fragments based on an initial examination of the separation data by the researcher (David C. Mansfield et al., "Automation of Genetic Linkage Analysis Using Fluorescent Microsatellite Markers," *Genomics*, Vol. 24, pp. 225–233, 1994). Although the final analysis is carried out by computer, there is still an initial screening step performed by the researcher.

The purpose of the initial screening is to eliminate from the automated analysis profiles of runs which were deemed by the user to be of unacceptable quality. A bad run can result from any of a number of sources of error. For example, impurities in the sample or undetectable levels of DNA would result in bad separation data. In the case where the genetic sample was good, the conditions of the separation run may have been compromised such as by the presence of a bad separation matrix or an improperly controlled electric field. The user must inspect the profiles and make a judgment call as to whether the data can be used for further analysis or whether the run needs to be repeated. The Mansfield et al. technique does not automatically provide this step, relying instead on the researcher's manual review of all data. Moreover, in the case of a good separation run, the Mansfield et al. technique and other methods in common practice still require the researcher to pull out certain information from the separation data and enter that information into the computer.

What is needed is a method for automated decision-making during certain phases in the analysis of a biochemical sample. More specifically, it is desirable to automate analysis of separation data so that a decision can be made as to a subsequent course of action in the analytical process. It is desirable to automatically ascertain the quality of a separation run before proceeding to the next step.

SUMMARY OF THE INVENTION

A method for performing a separation assay of a biochemical sample includes performing a separation run of the sample to produce separation data. The data is analyzed to produce a quality metric which is indicative of the quality of the separation run. The quality metric is then used to select a subsequent step in the assay, namely whether to proceed to a next step in the assay or to repeat the separation run. In the preferred embodiment of the invention, the quality metric is based on a measure of the resolution of the sample peaks in the data and on the signal-to-noise ratio of the data. In those cases, where a sizing standard is included in the separation run, the quality metric is further based on a measure of the degree of linearity of the reference peaks of the comigrating sizing standard. Performance of a comigrating quantitation or identification standard could also be used in separations.

In a particular example of the method, a genetic analysis includes selecting and amplifying a sample of DNA. The amplified product is labeled to mark target sequences of interest. An electrophoretic separation run is performed, including detecting signals indicative of the constituent components of the amplified material. The collection of signals (peaks) whose strength varies with time constitutes the separation data. This data is subsequently analyzed to produce a quality metric representative of the resolving power (quality) of the separation run.

Next, the quality metric is compared against two threshold values set to differentiate high-, marginal-, or low-quality separations. A first indicator is produced if the quality metric falls below a first threshold value, and similarly a second indicator is produced if the quality metric falls below a second threshold value (to differentiate marginal and poor samples). The first and second indicators respectively are thus FAIL and REVIEW indicators. A re-run of the sample is performed if the fail indicator is produced. A manual evaluation of the separation data is performed if the review indicator is produced. If the quality metric is greater than the second threshold, then the genetic analysis continues with a next step in the process, typically an allele calling step.

BRIEF DESCRIPTION OF THE DRAWINGS

FIGS. 5A–5B illustrate how the S/N ratio is computed.

BEST MODE FOR CARRYING OUT THE INVENTION

Figure 1:
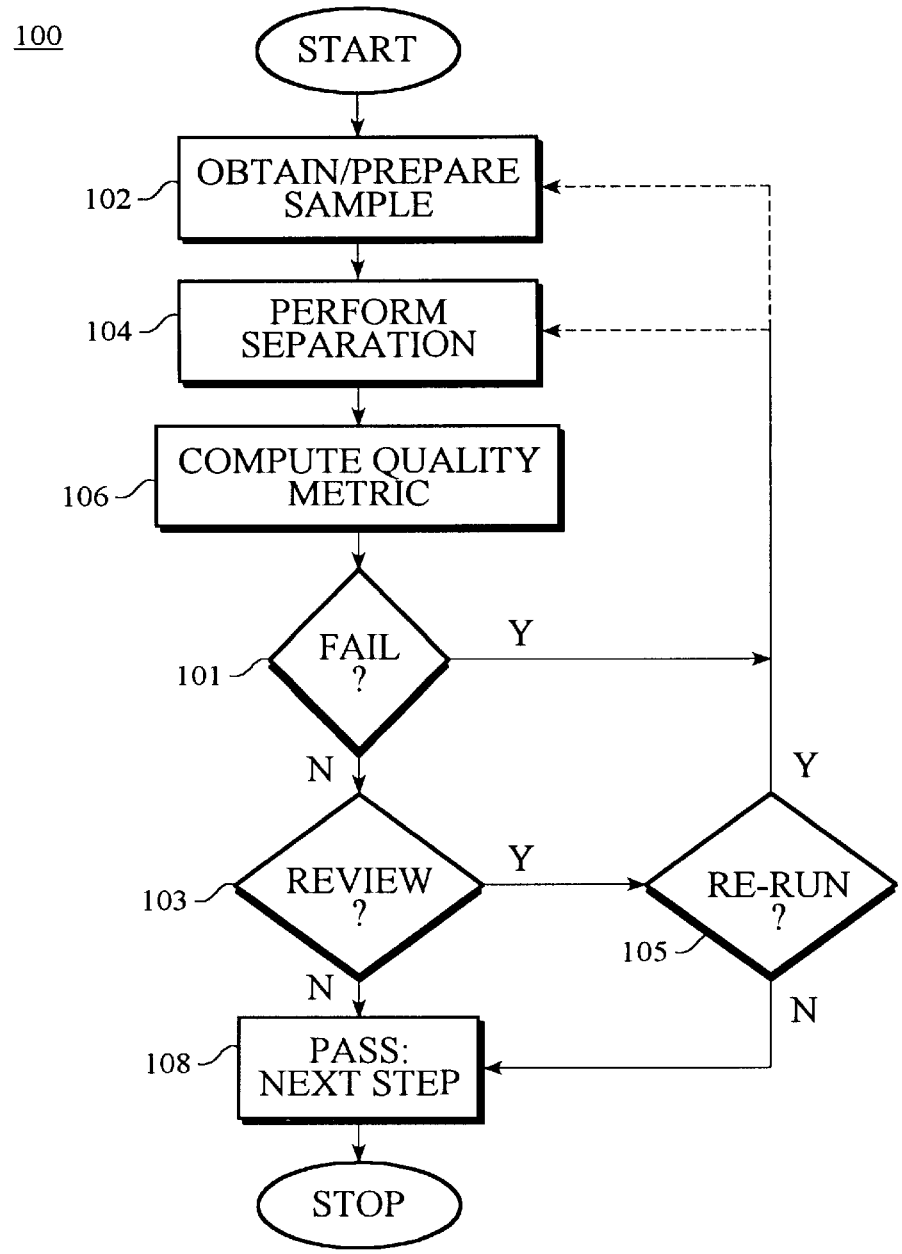
FIG. 1 is a flow chart showing the steps for a separation assay in accordance with the invention.

Referring first to the flow chart 100 shown in FIG. 1, the work flow of a separation assay in accordance with the invention includes the following steps: A biochemical sample is obtained and prepared, step 102. Next, a separation procedure on the sample is performed, step 104. The resulting separation data is then analyzed to produce a quality metric, step 106. The quality metric is then used to determine whether to repeat the separation (step 101), to visually inspect the separation data (step 103), or to proceed to the next step in the analysis of the sample, step 108. If visual inspection of the data is called for, then another decision is made based on the outcome of the visual inspection whether to repeat the separation (step 105) or to proceed to the next step in the analytical process, step 108.

The quality of the separation run is always important, since reliability in subsequent steps in the analysis depend on the quality of data obtained from the separation run. Prior art techniques require human screening of data before submitting the data for computer analysis. The development of a quality metric, the computation details of which will be discussed below, provides a standardized criterion by which to judge the "goodness" or the quality of the initial separation run. Moreover, the quality metric permits the use of computer-based analysis to initially sort through the voluminous data that can be generated in certain applications without human interaction, thus automating the process of analyzing the data; e.g. the Human Genome Project involves analyzing billions of base pairs comprising human DNA or millions of genotypes required to map the gene sequences.

As can be seen, since the invention centers around the use of a quality metric to judge the quality of the separation run and to control the work flow of the analytical process, the kind of biochemical sample being analyzed is irrelevant. For example, the analytical technique of the present invention can be used: to analyze foods for protein, fatty acid, and carbohydrate content; to separate carbohydrates, oligonucleotides and individual molecules such as nucleotides, amino acids, sugars, and biogenic amines; to separate and analyze pesticides and other synthetic organic molecules; to analyze drugs and pharmaceuticals; to analyze forensic and explosive compounds; to analyze serum organic acids, cyanide and related compounds, and chemical warfare compounds; to perform urinalysis for drug metabolites; and so on. The underlying principles of the invention apply to all separation process or assays.

The separation data produced by the various known separation techniques are similar in content and thus are readily subjected to processing under step 106. For example, capillary electrophoretic separations produce data that record detected signals (e.g. emissions from fluorescently labeled analytes) as a function of elution time. The time of occurrence of each peak in the data relates to the mass of the corresponding analyte. In gel-slab electrophoresis, the data comprises detection of analytes along a separation path in a gel. Here the data records detected signals as a function of distance from a starting point on the gel along the separation path. In this case, the distance of a peak value from the starting point relates to the magnitude of the electrical charge on the corresponding analyte. In general, separation of analytes will occur based on some physical property of the analytes, such as molecular mass or electrical charge. Similarly, the signals detected during the separation will be based on some physical property of the analytes. In the case of electrophoretic separations, for example, the detection property is fluorescence which is imparted to the analytes by the use of fluorescent labels.

In accordance with the invention, decision steps 101 and 103 consist of producing first and second indicators which assist the user in deciding a proper subsequent course of action. Thus, in step 101 a FAIL indicator is produced if the quality metric falls within a first range of values, informing the user that a particular run was deemed to be of low quality. In such a case, it is likely that the user will elect to re-run the separation, as indicated by the dashed line leading from decision box 101. Similarly, in step 103 a REVIEW indicator is produced if the quality metric falls within a second range of values to inform the user that a manual review of the data for the corresponding run is needed. The user can visually inspect the data, typically in the form of a graph such as an electropherogram, and decide whether a re-run is appropriate. Finally, for those runs which are deemed acceptable in quality, a PASS indicator is produced to inform the user that the analysis can proceed to the next step in the data analysis process, step 108.

A specific example of a separation assay in accordance with the invention will be given in order to provide context for a discussion of the quality metric. Keep in mind, however, that the practice of the invention is neither restricted to any one particular separation method nor limited to any one particular class of compounds to be analyzed.

Figure 2:
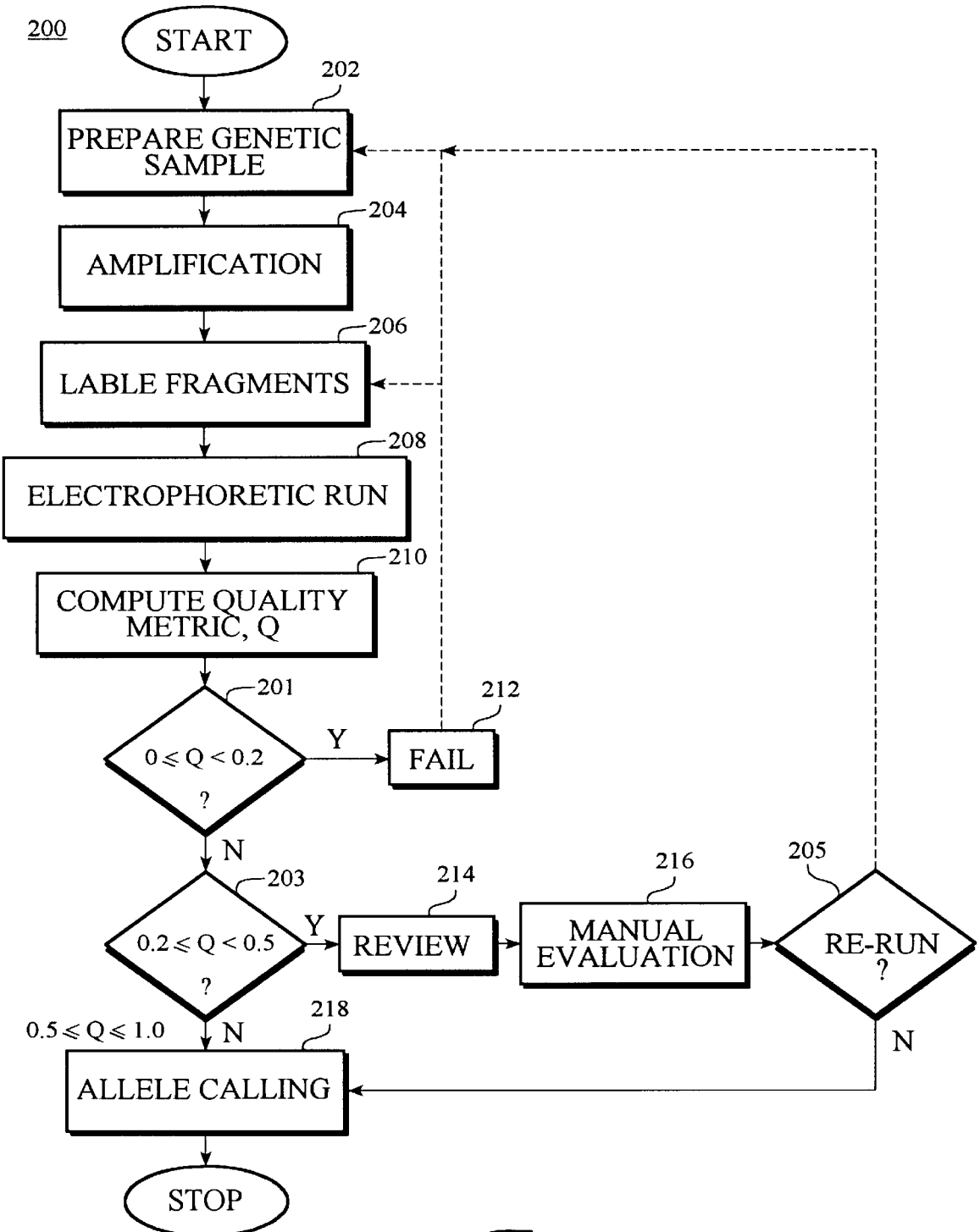
FIG. 2 shows a flow chart of the steps in an exemplary application of the present invention.

Referring then to FIG. 2, the work flow for gene fragment analysis is shown in flow chart 200. This procedure is used in the production of gene linkage maps, a first step toward the ultimate goal of identifying all the genes in human DNA.

First, a sample of polynucleotides (e.g. DNA, cDNA, and the various forms of RNA) is obtained, step 202. Next, copies of the sample are produced by a process known as amplification, step 204. Amplification of the genetic material can be achieved by any of a number of techniques, including in vivo cloning and polymerase chain reaction (PCR). Preferably PCR is used because the process is capable of high yields in a small amount of time. Target sequences in the amplified product are then labeled (step 206) by providing fluorescently labeled primers or substrates and enzymatic synthesis of DNA using PCR or other amplification process. The resulting labeled amplification products are then assayed according to the size of the constituent components, step 208. Numerous electrophoretic techniques are known, including slab-gel electrophoresis, capillary electrophoresis, and capillary array electrophoresis.

Each separation run of the labeled sample includes a co-migrating sizing standard with DNA fragments (markers) of known size. A unique label is used to differentiate the fragments in the DNA sizing standard from the components of the amplification products. A common technique is to use different fluorescent tags, one for the sizing standard and one for the amplification products. As the material migrates through the capillary or the slab-gel, an excitation source is used to induce fluorescence in the tags. The resulting emissions are collected by a nearby detector which produces a signal representative of the intensity of the detected fluorescence, and the resulting measurements are stored along with a time base to provide separation data representing intensity variations as a function of time.

From the separation data, a quality metric Q is computed, step 210. The quality metric is indicative of the quality of the separation run, and gives the researcher a quantitative basis for selecting a subsequent course of action. As can be seen in FIG. 2, the quality metric Q is compared against two sets of ranges, steps 201 and 203. In this example, if the computed metric for a particular run falls within the range 0.0 to 0.2, then the run will be marked with a FAIL indicator, step 212. If the computed metric falls within the range 0.2 to 0.5, then the run will be marked with a REVIEW indicator, step 214. If the computed metric is greater than or equal to 0.5, then the system will proceed to the next step in the process.

The quality metric, as will be shown below, is a real number between 0.0 and 1.0. Thus, the ranges used in steps 201 and 203 are defined by two threshold limits, namely 0.2 and 0.5. A separation run having a computed quality metric that falls below the first threshold of 0.2 indicates that the assayed sample has been compromised in some way, such as by the introduction of contaminants, improper preparation of the sample, or a contaminated separation matrix. Samples whose runs have a FAIL indication are likely going to have to be re-run. The dashed line leading from step 212 of flow chart 200 shows that a new sample may have to be prepared or that the same sample can simply be re-run, a choice to be made by the researcher.

A sample whose quality metric falls below the second threshold of 0.5, but not the first threshold of 0.2, indicates a low quality sample. However, the metric indicates that the sample nonetheless may contain at least a few loci that can be genotyped in a subsequent step in the process. The data for such runs, therefore, need to be manually evaluated (step 216) by the researcher to determine (step 205) whether a re-run is appropriate or if the data can be used in the next step of processing. Finally, a quality metric that lies above the second threshold will produce a PASS indicator, signifying that the data can proceed to the next step in the process. In this particular use of the invention, the data would automatically be routed to an allele calling analysis (step 220) in which alleles are identified from the data. A variety of allele calling algorithms are known, any one of which could be used in conjunction with the invention.

The thresholds are user-definable and can be modified as desired by the researcher. This permits the researcher to tailor the level of the quality of the separation runs for any given experimental situation.

The basic steps in a separation assay have been outlined in FIG. 1, showing that the use of a quality metric is easily incorporated in the process. FIG. 2 presents a typical application of the quality metric in gene analysis. The discussion will now turn to the quality metric itself.

Figure 3:
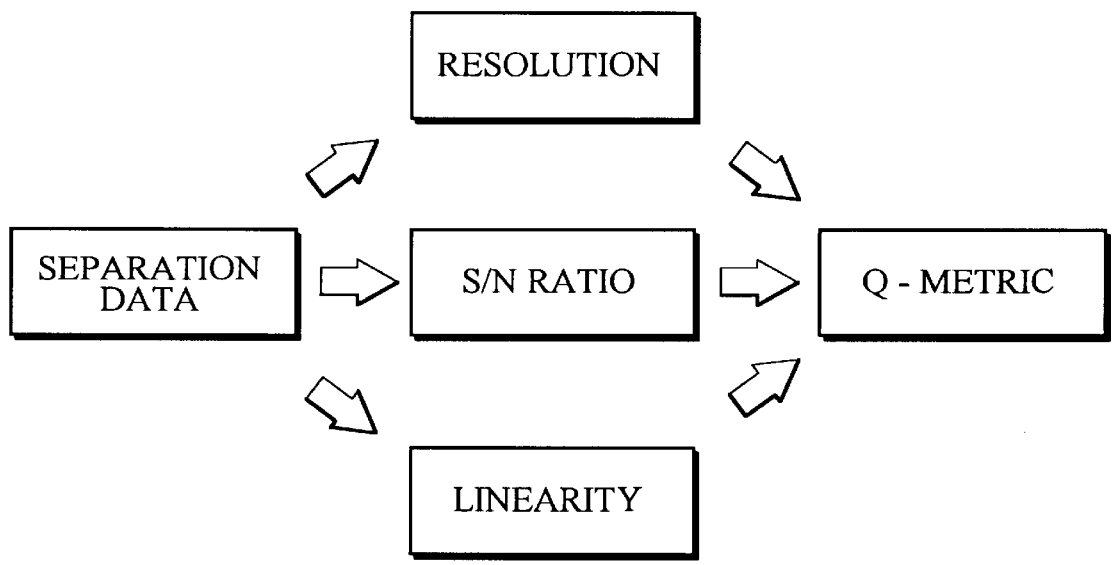
FIG. 3 shows the terms comprising the quality metric.

Referring to FIG. 3, it can be seen that the quality metric consists of terms derived from the separation data. First is a peak resolution term which is a measure of the overall resolution of the sample peaks detected during the separation run. Next is a signal-to-noise (S/N) ratio of the detected signals from the separation run. Finally, when a sizing standard is included in the run, a migration linearity index for reference peaks produced by the standard is computed. The terms are then combined to produce the quality metric Q.

Figure 4:
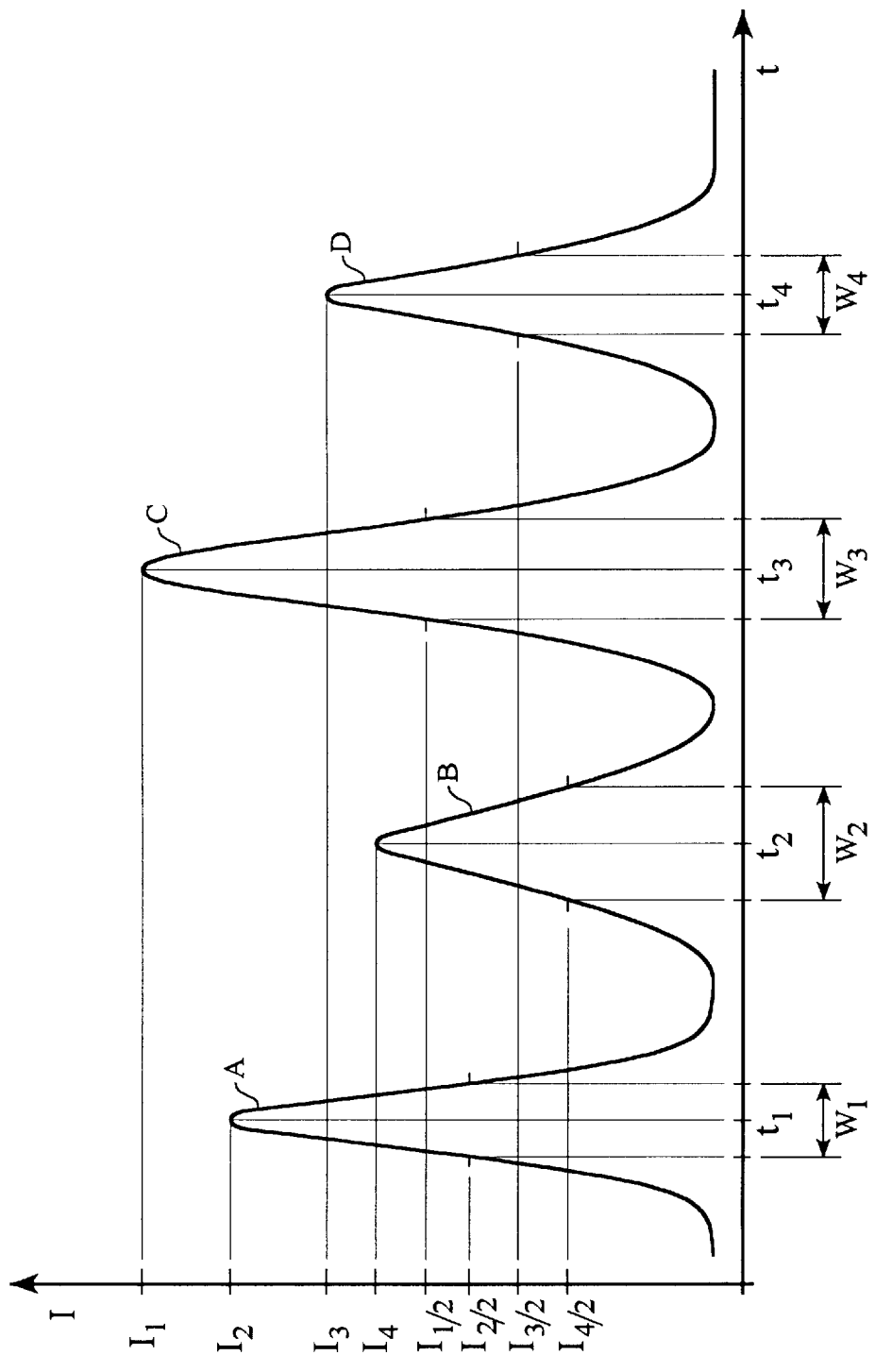
FIG. 4 is schematic representation of a typical electropherogram, illustrating how the peak resolution is computed.

First, the peak resolution term will be discussed with reference to FIG. 4 which is a schematic illustration of an electropherogram, showing exaggerated features in order to facilitate the explanation. The four peaks A–D represent sample peaks, having peak intensities $I_2$, $I_4$, $I_1$, and $I_3$ respectively and detection times $t_1$–$t_4$ respectively. FIG. 4 also shows bandwidths $W_1$–$W_4$, measured at the half-maximum intensity level of each peak.

In accordance with the present invention, the peak resolution term is computed by computing a resolution metric for each interior peak, i.e. those peaks other than the end peaks (peaks A and D). The resolution metric in the present invention is a measure which considers the two peaks adjacent to an interior peak. By comparison, the prior art resolution is a measure of the resolution between two peaks. Thus, for each interior peak the resolution metric includes data from the peak to its right and the peak to its left. The general equation is:

$$R = \frac{(t_n - t_{n-1})}{(w_n + w_{n-1})/2} + \frac{t_{n-1} - t_n}{(w_n + w_{n+1})/2} \qquad (1)$$

Thus, the resolution metrics $R_B$ and $R_C$ associated with interior peaks B and C are:

$$R_B = \frac{t_2 - t_1}{(w_2 + w_1)/2} + \frac{t_3 - t_1}{(w_2 + w_3)/2} \qquad (2)$$

$$R_c = \frac{t_3 - t_1}{(w_3 + w_2)/2} + \frac{t_4 - t_3}{(w_3 + w_4)/2}$$

As to end peaks A and D, the standard resolution calculation is used:

$$R_A = \frac{t_2 - t_1}{(w_1 + w_2)/2}, \qquad (3)$$

$$R_B = \frac{t_4 - t_3}{(w_4 + w_3)/2}$$

Finally, the peak resolution term is computed by taking the average of the individual resolution computations, namely $(R_A + R_B + R_C + R_D)/4$.

The next component of the quality metric, the signal-to-noise ratio (S/N), will now be discussed with reference to FIGS. 5A and 5B. Like FIG. 4, FIG. 5A is a schematic representation of an electropherogram showing exaggerated features of the data for a separation run of a sample. This computation involves two parts: computing the "noise level" in the separation data for the sample; and computing the "signal level" of the data.

Computation of the noise level will be discussed first. The separation data is first digitally pre-processed through a high pass filtering algorithm to flatten the baseline (removal of low frequency variation in the signal).

The amplitude of noise (noise level) is then determined by using a low pass filter algorithm. Generally, this involves looking at the percentile distribution of the signal amplitudes in the separation data. A plot of the percentile rank of each peak versus the numbers of such peaks in each percentile rank is plotted. The resulting curve exhibits a dramatic shift between a linear region of low intensity signals (i.e. the noise) and a narrow region of high intensity signals (i.e. the desired signals). A line tangent to the linear noise region is extended to intersect the percentile scale. The amplitude associated with the percentile rank at the intersection represents the amplitude of the observed noise in the separation data to be used in computing the quality metric.

Specifically, with reference to FIG. 5A, the maximum peak value from the data is determined, namely peak A2 having intensity $I_{max}$. The intensity scale in the data from zero to $I_{max}$ is then divided into N intervals. For each interval i, the upper bound is $I_{max}*(N-i+1)/N$ and the lower bound is $I_{max}*(N-i)/N$. Although N is equal to seven in the example shown in FIG. 5A, N is typically on the order of 100 or so and in general can be specified and subsequently modified by the user.

Referring to FIG. 5B, the number of peaks within each interval is determined as a function of the interval number. Thus, interval one brackets the intensity range from $I_{max}$ to $I_{max}*(N-1)/N$, and contains two peaks, A1 and A2. The second interval which brackets the intensity range from $I_{max}*(N-1)/N$ to $I_{max}*(N-2)/N$ also contains two peaks, B1 and B2. Interval number three includes one peak (C), interval number four includes four peaks (D1–D4), and so on.

A plot of peak-count versus interval-number, such as one shown in FIG. 5B, shows that there is a sudden increase in the number of counted peaks at some interval K. This represents a region in the separation data where the peaks are predominantly the result of noise. The cut off K represents the inflection point of the plot of peak numbers versus interval. It is the maximum first derivative of the curve.

Having determined the interval K, the noise level is computed as:

$$noise\ level = \frac{I_{max}}{N} * K \quad (4)$$

Next, the number of peaks in the intervals from 1 to K is determined and compared against a peak threshold M, thus:

$$\sum_{i=1}^{K} P_i < M, \quad (5)$$

where $P_i$ is the number of peaks in interval i.

The peak threshold, M, represents the minimum signal attributable to a peak (signal) and not to a high amplitude of noise. The peak threshold is user-selected and can be modified depending on the user's requirements.

If the total number of peaks occurring in intervals 1 through K is less than the peak threshold M, then the process is reiterated for intervals K through N. This amounts to dividing the data in the range from $I_{max}*(N-K+1)/N$ to zero into N intervals. Each interval in this iteration is bounded by upper and lower values, $I'_{max}*(N-K+1)/N$ and $I'_{max}*(N-k)/N$ respectively; where $I'_{max}$ is equal to the upper bound of interval K, namely $I_{max}* (N-K+1)/N$.

Another determination of peak-count versus interval number is made and a new interval K' is selected in accordance with the above criteria for selecting K. The noise level is re-computed as:

$$noise\ level = I'_{max}/N*K' \quad (6)$$

The peak threshold M again is compared against the peak count between interval 1 and the new interval K'. If the relation of Eqn. 5 still holds, then the process of subdividing is repeated once again, and continues until the relation in Eqn. 5 is no longer true, arriving at a "noise level" term that will be used in the S/N calculation.

The second term used in calculating the S/N ratio is the "signal level". The signal level is defined as the average peak height of those peaks in the separation data which are greater than (F * noise level), where F is a noise threshold.

F is a user selectable threshold for separating peaks from noise and where F>2. This cutoff threshold must exceed 2 because, in peak analysis, the limit of detection is generally defined as peaks with S/N>2.

Finally, the average observed peak signal is computed by:

$$S/N = \left(\frac{1}{n}\sum_{i=1}^{n} H_i\right) / noise\ level, \quad (7)$$

where $H_i$ is the peak height of the peaks used in the signal level term, and n is the number of such peaks.

Figure 6:
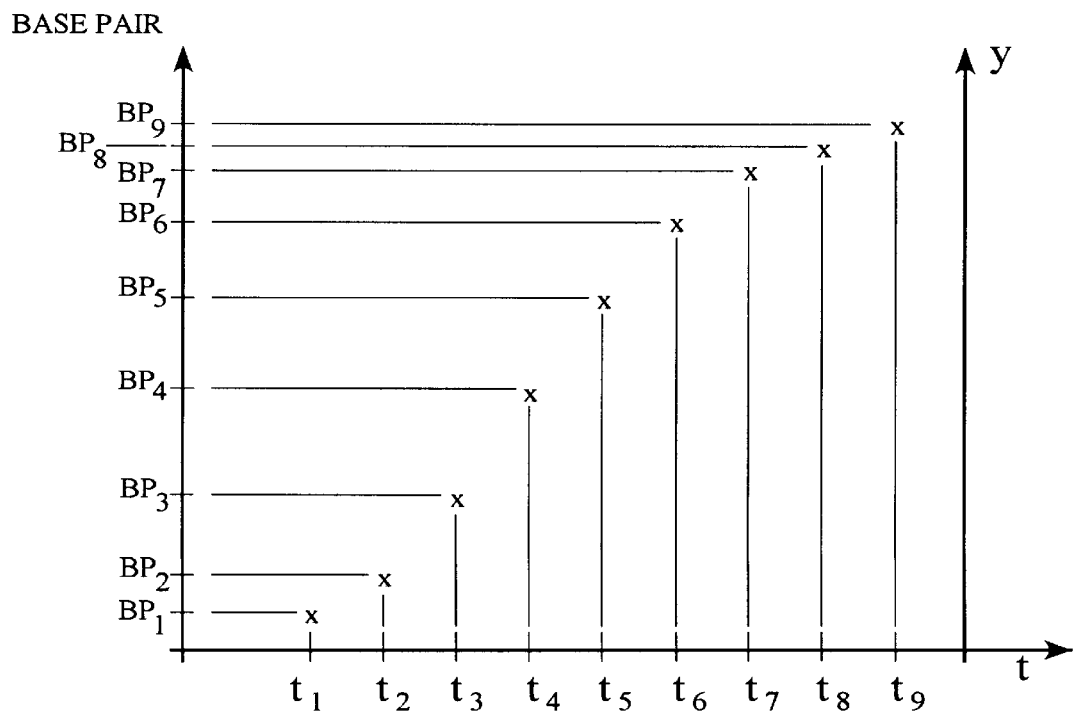
FIG. 6 shows a graph of a sizing standard illustrating how the information is used in determining the linearity index.

The third component of the quality metric is the linearity index of a sizing standard. The sizing standard provides a basis for converting peak detection times of the sample peaks to a corresponding measure of size, such as number of base pairs or molecular weight. For example, in an electrophoretic separation of polynucleotides, a sizing standard may include marker peaks having nucleotide chains of 100 base pairs, 200 base pairs, and 400 base pairs in length. The elution times of these markers might be 10 minutes, 20 minutes and 40 minutes respectively. A co-migrating sample which has a peak at 30 minutes would be estimated to be 300 base pairs long by interpolating between flanking markers at the 20 and 40 minute peaks of the sizing standard. The accuracy of the interpolation depends on the linearity or fit to a third order curve of the size-time relation of the sizing standard; not all separations are linear, but can be fit to second, third or higher order curves more precisely. The linearity index of the sizing standard therefore serves as a measure of the degree of linearity or precision of fit to a third order curve of the size/time relation, and is arrived at in the following manner:

First, the sizes of the constituent markers in the sizing standard and their corresponding elution times are obtained. The first peak in the data for the standard corresponds to detection of the smallest marker, since it will elute first. The size (i.e. number of base-pairs) for the smallest marker corresponds to the time of occurrence of the first peak. Likewise, the next larger marker in the standard will appear at a time corresponding to the time of occurrence of the second peak, and so on. A graph of this relation is shown in FIG. 6, where base pair length ($BP_i$) is plotted as a function of elution time ($t_i$). In the gene analysis example, the standard is a collection of nucleotide marker fragments and the "size" of each fragment is expressed in terms of base pairs. For other separation assays, the "size" of the constituents in a standard might refer to some other physical property of the constituents such as molecular weight.

Next, using a least squares technique the points from the data are approximated by a third order polynomial. While other interpolation methods are possible, it has been observed that a third order curve showed the best performance over the full range of sizes (i.e. base pairs) in the sizing standard. More specifically, a third order polynomial $y(t_i)$ is selected such that $$\sum_{i=1}^{N} (y(t_i) - BP_i)^2 \qquad (8)$$

is minimized.

The linearity index is then computed as:

$$\text{linearity index} = 1 - \sqrt[4]{1 - R^2}, \qquad (9)$$

where $R = 1 - \dfrac{\sum_{i=1}^{N} y(t_i)^2 - BP_i^2}{\sum_{i=1}^{N} BP_i^2 - \dfrac{(\sum BP_i)^2}{N}}$, and N is the number of constituents in the standard.
Finally, the quality metric Q is computed as follows:

$$Q = \frac{(a * \text{linearity index}) + (b * S/N) + (c * \text{peak resolution})}{a + b' + c} \qquad (10)$$

where (11)
  $a$ is in the range of 2 to 10,
  $b$ is in the range 0.1 to 1.0,
  $c$ is in the range 0.5 to 2.0, and
  $b' = \begin{cases} b * S/N & \text{if } S/N > 40 \\ b * 40 & \text{otherwise} \end{cases}$ The scaling constants a, b, and c are user selectable, with default values of a=5, b=0.2, and c=1.0 for capillary separations. The range and default values can be adjusted to other types of separation depending on what signal intensity and resolution is observed in the process.

While the above-discussion has focused on capillary electrophoretic (CE) separations, recall that the method is equally applicable to other kinds of separation assays. For example, gel separations generate data where peak detection is distance-based rather than time-based. However, gel image data is subject to the same kind of analysis as electropherograms, except that a distance measurement is replaced for time. In chromatographic separations, like CE separations, the analyte passes a fixed detector and signal intensity versus time is measured.

Figure 7A:
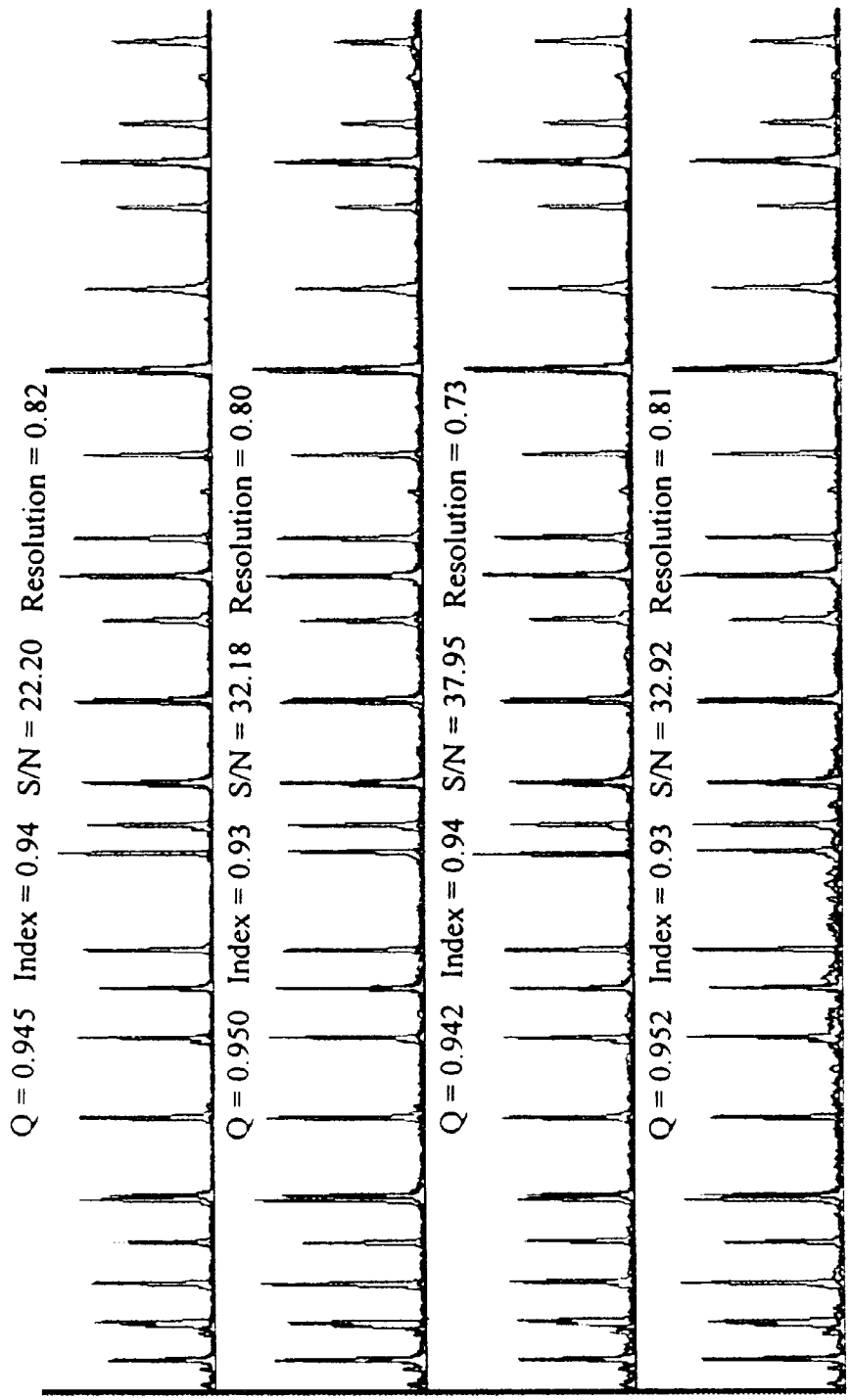
FIGS. 7A and 7B show the invention reduced to practice in the analysis of DNA fragment separations. High quality separations (FIG. 7A) obtain high Q scores, while poor quality samples are sorted based on their lower scores (FIG. 7B).
Figure 7B:
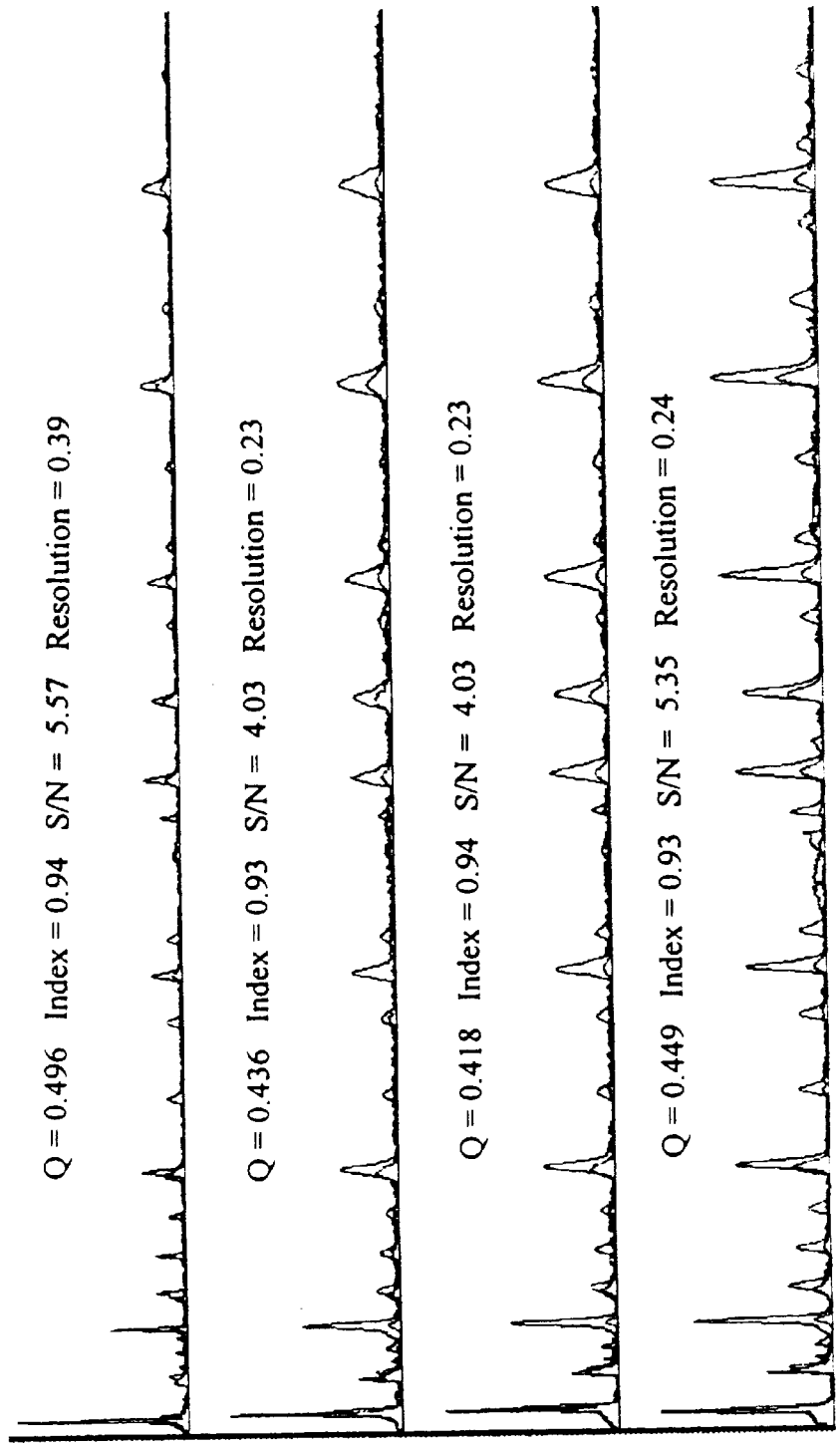

The method of the invention is readily reduced to practice in the form of a computer system running software which implements the steps comprising the method and illustrated in FIGS. 7A and 7B. In a run of 96 capillaries, the same amount of DNA was separated. Most of the separations were of high quality as shown by the four capillaries with the highest Q metric (FIG. 7A). Poor quality separations result in broad, weak peaks as evidenced in the capillaries with the lowest Q metric (FIG. 7B). The implementation of the software is well within the scope of the average programmer of ordinary skill. In addition, the software can be incorporated in a semi-automated system which uses robot manipulators to prepare the samples and perform the separation runs. The PASS, FAIL, and REVIEW indicators would consist of signals transmitted to robotic controllers to operate the manipulators to perform various tasks according to the invention. Thus, samples having FAILed runs could be automatically re-run, while sample runs identified for REVIEW would be sent to the researcher for manual inspection.

The particular computations disclosed above set forth the best mode of carrying out the invention as contemplated by the inventors. However, it should be appreciated that the separation data can be subjected to other analyses which also are indicative of the quality of the separation and which can be used to direct the course of action subsequent to the separation run, without departing from the scope and spirit of the present invention.

We claim:

1. A method of analyzing a biochemical sample, comprising:
   in a separation run, separating the sample into its constituent components thereby producing separation data representing detection of a signal indicative of a physical property associated with the components as a function either of time or of distance along a separation path, the separation data having a plurality of sample peaks;
   separating a co-migrating standard having constituents of known physical properties thereby introducing reference peaks into the separation data;
   based on the separation data, computing a quality metric indicative of the quality of the separation run including computing a value indicative of the resolution of the sample peaks in the separation data, computing a value indicative of a signal-to-noise ratio in the separation data, and determining a decree of linearity of the reference peaks; and
   based on the quality metric, either proceeding with a next step in analyzing the sample or repeating the separation run.

2. The method of claim 1 further including:
   comparing the quality metric against a first threshold value;
   if the quality metric is less than the first threshold then producing a first indicator;
   if the quality metric is greater than or equal to the first threshold then comparing the quality metric against a second threshold value;
   if the quality metric is less than the second threshold then producing a second indicator; and if the quality metric is greater than or equal to the second threshold then producing a third indicator.

3. The method of claim 2 further including repeating the separation run if the first indicator is produced.

4. The method of claim 3 further including manually inspecting the separation data if the second indicator is produced and repeating the separation run based on results from the step of manually inspecting the separation data.

5. The method of claim 4 further including proceeding with the next step in the analysis if the third indicator is produced.

6. The method of claim 1, wherein the biochemical sample is a biological monomer selected from the group comprising amino acids, nucleotides and sugars, and biological polymers including DNA, RNA, peptides, and carbohydrates, and wherein the step of separating the sample includes one of electrophoretic separation, column chromatography, high performance liquid chromatography, and isoelectric focusing.

7. A method for analyzing polynucleotides, comprising:
making copies of a sample of polynucleotides to produce amplification products;
labeling a target sequence in the amplification products;
mixing a sizing standard with the amplification products;
in a separation run, separating the amplification products including detecting signals indicative of constituents of the amplification products and producing data representing variations in the detected signal as a function either of time or of distance along a separation path, the data including reference peaks indicative of the separation of the sizing standard;
computing a quality metric indicative of the quality of the separation run, the quality metric being a function of the data, the step of computing including computing a resolution of peak values in the data, computing a signal-to-noise ratio of the data, and computing a degree of migration linearity of the reference peaks; and
based on the value of the quality metric, producing a first indicator if the quality metric is less than a first threshold and producing a second indicator if the quality metric is greater than the first threshold and less than a second threshold.

8. The method of claim 7 further including repeating the separation run when the first indicator is produced, and manually evaluating the data when the second indicator is produced to determine whether to repeat the separation run.

9. The method of claim 7 further including producing a third indicator if the quality metric is greater than the second threshold.

10. The method of claim 9 wherein the polynucleotides constitute genetic material; the method further including identifying alleles from the data when the third indicator is produced.

11. The method of claim 7 wherein the step of separating is either capillary electrophoretic separation or capillary array electrophoretic separation, and wherein the data is an electropherogram profile.

12. The method of claim 7 wherein the step of separating includes slab-gel electrophoretic separation, and wherein the data is obtained from a gel image.

13. The method of claim 7 wherein the step of amplifying is a step of amplifying by polymerase chain reaction.

14. A method for a separation assay of genetic material, comprising the steps of:
amplifying and labeling the genetic material to produce amplification products;
mixing a sizing standard with the amplification products;
in a separation run, electrophoretically separating the amplification products and the sizing standard to separate out constituent components thereof;
detecting a signal indicative of the constituent components and producing separation data representing variations in the detected signal versus time, the separation data including peak values which correspond to sizes of the constituent components;
computing a quality metric indicative of the quality of the separation run, including computing a resolution of the peak values, computing a signal-to-noise ratio of the separation data, and computing a degree of migration linearity of those peaks which correspond to constituent components of the sizing standard; and
based on the value of the quality metric (i) proceeding with a next step of the analysis, (ii) manually evaluating the separation data to determine whether to repeat the separation run, or (iii) repeating the separation run.

15. The method of claim 14 wherein the next step is a step of identifying alleles from the separation data.

16. The method of claim 14 wherein if the quality metric falls within a first range of values then repeating the separation run.

17. The method of claim 16 wherein if the quality metric falls within a second range of values then manually evaluating the separation data to determine whether to repeat the separation run.

18. The method of claim 17 wherein if the quality metric falls within a third range of values then identifying alleles from the separation data.

19. The method of claim 14 wherein the step of separating includes one of slab-gel electrophoretic separation, capillary electrophoretic separation, and capillary array electrophoretic separation, and wherein the separation data is an electropherogram profile.

20. The method of claim 14 wherein the step of amplifying is a step of amplifying the selected portion of the genetic material by polymerase chain reaction.

21. The method of claim 14 wherein the step of amplifying is a step of cloning the selected portion of the genetic material.

* * * * *